United States Patent [19]
Landis

[11] Patent Number: 4,900,253
[45] Date of Patent: Feb. 13, 1990

[54] DENTAL MIRROR HAVING ULTRAVIOLET FILTER

[76] Inventor: Timothy J. Landis, 4532 Las Encinitas, Fair Oaks, Calif. 95628

[21] Appl. No.: 73,700

[22] Filed: Jul. 15, 1987

[51] Int. Cl.⁴ .............................................. A61B 1/24
[52] U.S. Cl. ................................ 433/30; 250/504 H; 350/640; 350/642; 350/1.5
[58] Field of Search .................... 433/30, 31; 350/640, 350/642, 1.1, 1.5, 1.6, 1.7; 250/504 R, 504 H; 128/10, 11

[56] References Cited

U.S. PATENT DOCUMENTS

| 3,162,191 | 12/1964 | Canan | 433/30 |
| 4,592,726 | 6/1986 | Brilliant | 433/30 |
| 4,640,685 | 2/1987 | Croll | 433/141 |
| 4,662,842 | 5/1987 | Croll | 433/141 |

FOREIGN PATENT DOCUMENTS

| 0481075 | 2/1952 | Canada | 350/1.7 |
| 0113421 | 6/1984 | Japan | 350/601 |
| 0306722 | 2/1929 | United Kingdom | 433/31 |

Primary Examiner—Gene Mancene
Assistant Examiner—Adriene J. Lepiane
Attorney, Agent, or Firm—Julian Caplan

[57] ABSTRACT

A dental mirror is modified to provide an orange filter to block ultraviolet or blue light from a light source frequently used to cure plastic tooth filling materials. Various filter means are disclosed. Thus the glass of a dentist's hand held mirror may be colored orange or amber and the front surface may be a two-way mirror. Second, the clear glass of the mirror may be backed by a transparent plastic colored orange or amber, the front surface being a two-way mirror. Third, a bottomless mirror may be coated on its back surface with a chemical deposit which absorbs ultraviolet and blue light. These are some of several alternatives described. The mirror may be used in the same manner as conventional mirrors. When the dentist illuminates the ultraviolet lamp to cure plastic fillings, the filter is interposed between the light source and the eyes, preventing damage to the retinas which might otherwise occur. The present invention allows the user to monitor the relationship between the light-curing light and the material being cured in the tooth during the curing procedure.

3 Claims, 2 Drawing Sheets

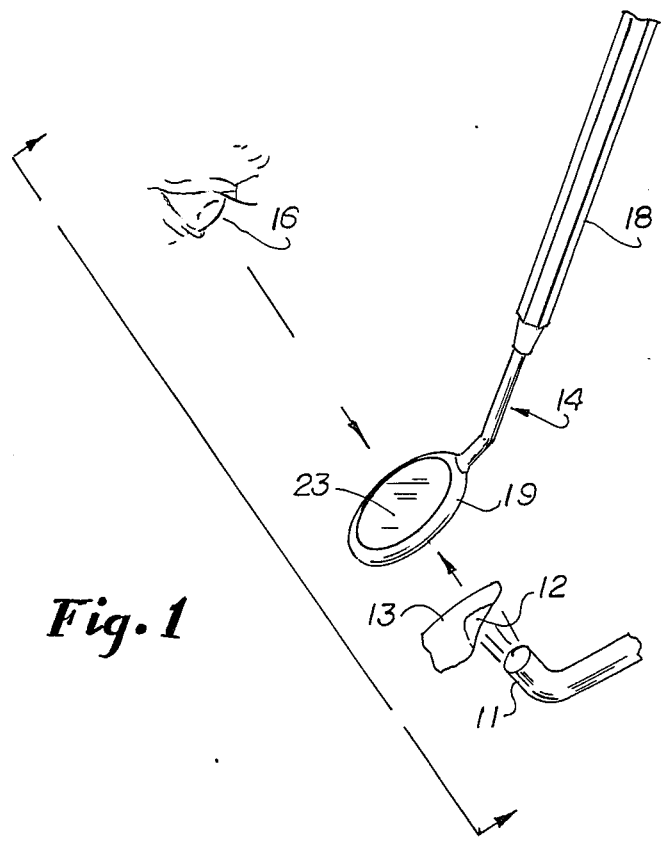
Fig.1
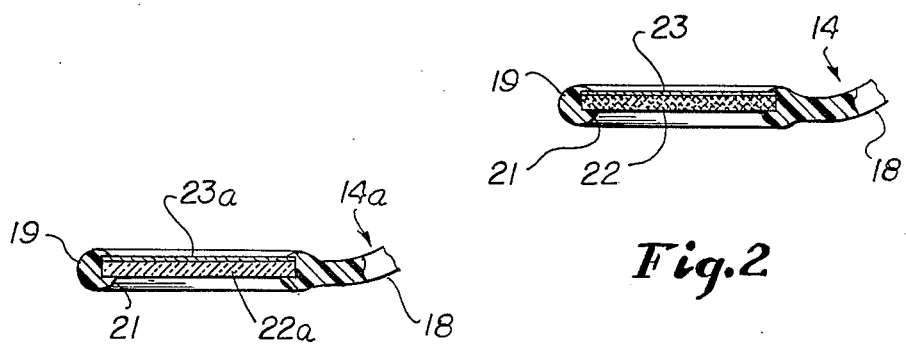
Fig.2
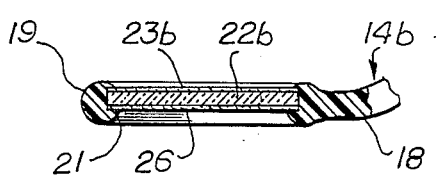
Fig.3
Fig.4

DENTAL MIRROR HAVING ULTRAVIOLET FILTER

BACKGROUND OF THE INVENTION

1. Field of the Invention

This invention relates to a new and improved dental mirror having ultraviolet filter means incorporated therein so as to reduce the impingement upon the retina of the dentist or dental technician of the ultraviolet and/or blue light emitted from a light source used to cure plastic or composite tooth filling materials.

2. Description of Related Art

There are many products on the market made of clear amber colored plastic or glass used to shield the eye from the intense blue or ultraviolet light used for light curing composites used as tooth filling materials. Among these products are those employing a large, flat paddle-shaped disc, similar to a ping pong paddle, made of amber colored plastic or glass. Additionally eyeglasses of orange glass or plastic are used. Orange plastic nipples which fit on the end of the light emitting fiber optic and confine the emitted light to the composite material are also used. Some dentists and technicians use eyeglasses with orange lenses or clip-ons to regular eyeglasses. The present invention is an improvement on all of these prior means for shielding the eyes.

SUMMARY OF THE INVENTION

The present invention uses a hand held dental mouth mirror of otherwise conventional shape as an instrument to shield blue or ultraviolet light. A conventional hand held mirror uses a glass blank, the back or front surface of which is mirrored. One of the features of the present invention is the use of a "two-way" mirror and the incorporation in the mirror of the filter heretofore described. Thus, the glass of the mirror may be orange or clear. They may then be coated or otherwise rendered absorptive of blue or ultraviolet light. Orange acetate filters, orange clear plastic mirror handles and ultraviolet absorbing chemicals may be used to coat glass or plastic.

The mirror has a glass blank which may be either orange or clear. Most dental mirrors use a metal oxide such as an oxide of indium which is applied to one of the glass surfaces. The glass is then mounted in a metal or plastic opaque bracket and handle. The metal oxide is applied to the glass surface indiscriminately. In the present invention the thickness of the metal oxide coating is controlled so that the mirror is made "two-way" so that it reflects only a percentage of the light which falls onto it, such as 75-99%. Thus the present mirror will reflect light when it is being used in the conventional manner. It will also transmit a portion, but only a portion, of the blue light from a fiber optic light pipe when it is interposed between the source of light and the dentist's eye thereby enabling the dentist to observe the proper placement of the light pipe relative to the composite filling material being cured but still block sufficient light so that the eyes are not damaged.

Other objects of the present invention will become apparent upon reading the following specification and referring to the accompanying drawings in which similar characters of reference represent corresponding parts in each of the several views.

FIG. 1 is a schematic perspective view showing one form of the invention in position of use.

FIG. 2 is an enlarged fragmentary sectional view through the mirror of FIG. 1.

FIGS. 3–8 inclusive are views similar to FIG. 2 of modifications of the invention.

Figure 9:
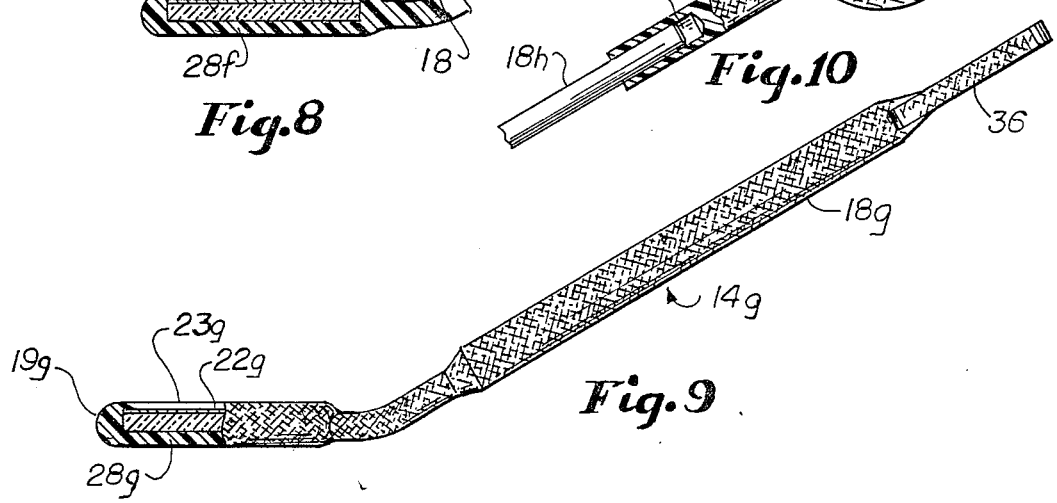

FIG. 9 is a side elevational view partially broken away to reveal internal construction of still another modification.

Figure 10:
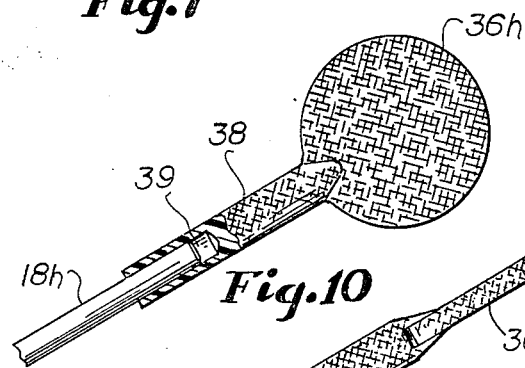

FIG. 10 is a fragmentary view partially broken away in section to reveal internal construction showing the filter mounted as a paddle on the proximal end of the handle of a conventional mirror.

DESCRIPTION OF THE PREFERRED EMBODIMENTS

Directing attention to FIG. 1, there is shown a light pipe of fiber optic material 11 from which is emitted ultraviolet or blue light. This light is used to cure the composite filling material 12 which is deposited in a tooth 13. Mirror 14 is interposed between the light source 11 and the eye 16 of the dentist or dental technician. In the form of the invention shown in FIG. 1 the mirror 14 is being used as a filter to screen from the eye most of the harmful light emitted from the source 11 while still permitting the dentist to observe through the mirror 14 the positioning of the light source 11 relative to the filling material 12. The mirror 14 may be used in a manner similar to other mirrors when the light source 11 is not being used. Thus, the mirror surface of the instrument may be positioned behind the tooth 13 and used to observe the back of the tooth in conventional manner. The present invention illustrates a number of different constructions of the mirror 14.

Thus directing attention to FIG. 2, mirror 14 has a handle 18 of metal or plastic formed with a circular rim or bracket 19. In the form of the invention shown in FIG. 2 the back of the bracket 19 is open as illustrated by the open bottom 21. Installed in the bracket 19 is a glass or plastic blank 22 which in the form of the invention shown in FIG. 2 is orange in color so as to absorb the ultraviolet or blue light emitted from the source 11. Formed on the upper surface of the glass 22 is a metal oxide mirror deposit 23 of indium oxide or other suitable material which is so deposited that it constitutes a two-way mirror in that some of the light emitted from the source 11 when the mirror is held in the position of FIG. 1 reaches the eye 16 so as to enable the dentist to ensure that the light source 11 is properly positioned relative to the composite material 12. On the other hand, when the mirror is used behind the tooth in the manner of a normal mirror, the surface 23 is sufficiently reflective so that the mirror may be used in normal fashion.

The orange or amber colored glass must have the ability to reflect light which falls on it in the range of 25 to 99%. It also must have the ability to transmit light in the range of 50% to ¼%. However, it filters out the blue and ultraviolet wavelengths by reason of the fact that the glass is orange colored.

Directing attention to FIG. 3, the glass 22a is clear and thus there is no filtering of the blue light per se. However, all wavelengths are attenuated—i.e., transmitted but at a very low intensity. At such low intensities the blue light is not harmful to the retina.

In FIG. 4 the glass 22b is clear. However a clear chemical coating 26 is applied to the back surface of the glass 22b which absorbs ultraviolet and blue wavelengths of light. The chemical coating may be applied to either side of the mirror.

Figure 5:
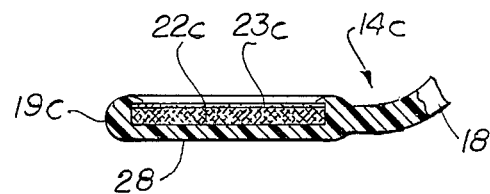

FIG. 5 differs from FIG. 2 in that instead of the bottom of the rim 19 being open, the backing 28, preferably of clear plastic, which is integral with rim 19c, protects the back surface of the mirror. The amber glass 23c absorbs the undesired light wavelengths.

Figure 6:
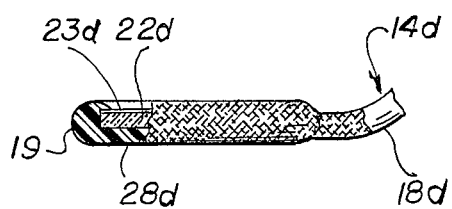

FIG. 6 is similar to FIG. 5 except that instead of the backing 28d, handle 18d and rim 19c being of clear plastic, in the modification of FIG. 6 the handle 18d, rim 19, and backing 28d are molded of an orange plastic and the glass 22d is clear. Thus the backing 28d absorbs the undesired wavelengths.

Figure 7:
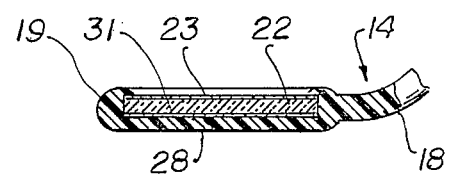

In FIG. 7 an orange acetate filter 31 is interposed between the clear glass 22 and the clear backing 28. The acetate or other filter 31 absorbs the undesired light wavelengths.

Figure 8:
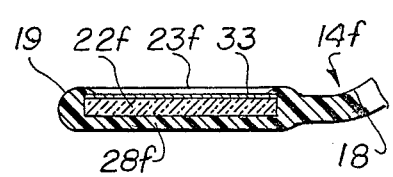

In FIG. 8 a chemical coating 33 is applied to the glass 22f to absorb the undesired wavelengths. This coating 33 is shown on the top surface of the glass blank 22f but could be on the back of the blank or could be o the backing 28f.

The modification of FIG. 9 has a paddle 36 at its proximal end which may be positioned between the light source and the eye when the light source is being used but in other instances the mirror is used in the same manner as conventional dental mirrors. Preferably the entire handle 18g, rim 19g, backing 28g and paddle 36 are molded of orange or amber plastic.

In the form of the invention shown in FIG. 9, the paddle 36 is molded integral with the handle 18g. In FIG. 10 the paddle 36h, molded of orange or amber plastic is formed with a stem 38 which is formed with a bore 39 so that the upper end of a conventional mirror handle 18h may be inserted in the bore 39.

The modifications of FIGS. 3–10 resemble preceding modifications and the same reference numerals followed by subscripts a, b, c, d, e, f, g, and h are used to indicate corresponding elements in FIGS. 3–10, respectively.

As used herein, the term "mirror" is preferably of a two-way type which reflects light impinging on the front thereof but also transmits a portion of the light impinging on the back. "Ultraviolet" means radiation of that wavelength range and also visible light of longer wavelength. "Orange" means those colors which absorb some, but not all, of the ultraviolet wavelengths.

What is claimed is:

1. A hand-held dental mirror for use both as a mirror and as a filter of light in the ultra violet range comprising a handle, a rim at a first end of said handle, mirror means held by said rim, said mirror means comprising a blank, a coating on at least one surface of said blank characterized by its ability to transmit a portion of light and to reflect a portion of light and filter means incorporated in said blank absorbing transmission of a portion of said ultra-violet range through said mirror means, said coating and said filter means being substantially congruous with said mirror means.

2. A mirror according to claim 1 in which said mirror means comprises a blank of glass, said glass being colored orange to absorb transmission of said portion of said ultraviolet range.

3. A mirror according to claim 1 in which said filter means is orange.

* * * * *